United States Patent Office

Re. 26,883
Reissued May 19, 1970

26,883

PROCESS FOR THE REDUCTION OF THE AROMATIC CONTENT OF PETROLEUM DISTILLATES

Joseph Eugene Marcel Marechal, Watermael-Boitsfort, Henri Robert Debus, Meise, and Raymond Marc Cahen, Woluwe-St. Pierre, Belgium, assignors to Labofina S.A., Bruxelles, Belgium No Drawing. Original No. 3,269,939, dated Aug. 30, 1966, Ser. No. 357,317, Apr. 3, 1964. Application for reissue Aug. 26, 1968, Ser. No. 760,385
Int. Cl. C10g *23/04;* C07c *5/02*
U.S. Cl. 208—143 11 Claims

Matter enclosed in heavy brackets [ ] appears in the original patent but forms no part of this reissue specification; matter printed in italics indicates the additions made by reissue.

*ABSTRACT OF THE DISCLOSURE*

*This invention is directed to a process for the reduction of the aromatic content of petroleum distillates having a high sulphur content by hydrogenating with a platinum catalyst upon a silica and alumina carrier, each in major quantity.*

Petroleum distillates boiling within the range of about 60° C. to about 350° C. and used either as jet fuels or as fuel oils or as solvents and the like, contain aromatic hydrocarbons which are harmful in certain cases.

The heat of combustion of a hydrocarbon is proportional to the hydrogen to carbon ratio, so that its value will be higher for a saturated cyclic hydrocarbon than for the corresponding aromatic hydrocarbon. Moreover, the lower the aromatic content of the fuel, the cleaner and the less harmful will be the combustion thereof. It is also desirable to remove aromatics from illuminating oils and stove oils to reduce the evolution of smoke. Still further, the reduction of the aromatic content of some solvents is of great importance on hygenic grounds since the vapors of aromatic hydrocarbons are toxic.

Several methods are known for the reduction or the complete elimination of aromatic hydrocarbons from petroleum distillates, such techniques as sulphuric acid refining, solvent extraction with sulphur dioxide, adsorption on a solid adsorbent or catalytic hydrogenation. The first three methods separate a fraction rich in aromatic hydrocarbons and therefore present the disadvantage of lowering the yield of the refined product. Such is not the case with catalytic hydrogenation which moreover presents the advantage of simpler processing and is therefore more economical.

Several types of catalysts may be used for saturating mono- and polycyclic aromatics, for example, nickel on kieselguhr or silica, nickel and tungsten sulphides, and noble metals such as platinum.

The use of nickel as a catalyst permits the reaction to be carried out under relatively moderate conditions of temperature and pressure. However, its use presents two major inconveniences. Firstly, nickel is very sensitive to sulphur-containing compounds and the poisoning resulting from their presence in the feed is irreversible. And secondly, nickel may not be heated above about 400° C. without losing its catalytic activity. The catalyst activity drops continuously as sulphur-containing compounds accumulate thereon; and the lack of heat stability of the nickel catalyst does not allow the regeneration of the catalytic activity by the combustion of these poisons.

Nickel and tungsten sulphides in well defined ratios and deposited on a convenient carrier such as alumina, or without carrier, may also be used as catalysts. These sulphides present the advantage of being insensitive to sulphur-containing compounds but are, however, far less catalytically active than the corresponding pure metals. The operating conditions must therefore be more severe, i.e. a higher temperature, lower space velocity and especially, a higher pressure are required. This last condition is essential as satisfactory results can be obtained only at higher pressures, on the order of 100 kg./cm.$^2$ and upwards.

Platinum, on the other hand, does not present the disadvantages inherent in nickel and tungsten sulphides as will appear in the following examples. Platinum catalysts, however, are poisoned by sulphur. Their use thus requires a very considerable and important diminution of the sulphur present in the feed in order to permit the hydrogenation to be carried out during long periods of time without having to regenerate the catalyst.

The principal advantage of this invention, therefore, is to provide an improved hydrogenation process for the reduction of aromatics in a petroleum distillate.

Upon further study of the specification and claims other objects and advantages of the present invention will become apparent.

These objects are attained by the discovery that much higher values of the sulphur content of the charge may be tolerated if platinum is supported on silica-alumina rather than on alumina alone.

According to the present invention there is provided a continuous process for lowering the aromatic hydrocarbon content of a petroleum distillate boiling between 60° C. and 350° C., whose sulphur content is previously adjusted, using a platinum on silica-alumina catalyst in the presence of hydrogen under pressure, at a temperature and a liquid space velocity determined according to the desired degree of aromatic hydrogenation and the sulphur content of the charge.

In general, the petroleum distillates of this invention usually contain as a matter of practice a minimum of 0.1 p.p.m. by weight of sulphur, and an aromatic content of about 1 to 99% by volume.

More particularly, according to the invention, there is provided a continuous method for reducing the aromatic hydrocarbon content of a petroleum distillate having a sulphur content preferably not greater than 300 p.p.m. by weight and boiling in the range of 60° C. to 350° C., comprising hydrogenating said petroleum distillate in the presence of a catalyst, comprising platinum on a silica-alumina catalyst carrier which contains at least 75% by weight of silica.

The influence of the catalyst carrier might be explained by more or less pronounced activity towards the destructive hydrogenation of sulphur-containing molecules. This explanation is purely theoretical and cannot be regarded as in any way limitative of the invention. The catalyst preferably contains between 0.1 and 1% platinum by weight, and even more preferably 0.3 to 0.8% by weight. Preferably the silica content of the catalyst carrier is from 75% to 90% by weight.

Hydrogenation is desirably carried out under the following conditions:

Temperature: 100 to 400° C., preferably 250 to 350° C.
Space velocity: 0.1 to 20 v./v./hr., preferably 0.5 to 10 v./v./hr.
Pressure: 5.0 to 70 kg./cm.$^2$, preferably 20 to 55 kg./cm.$^2$ (70 to 1000 p.s.i.g.) (300 to 800 p.s.i.g.)
Hydrogen to hydrocarbon ratio: 100 to 3,000 liters hydrogen at normal temperature and pressure (N.T.P) per liter of liquid feed, preferably 150 to 2,500 liters hydrogen—in English units about 500–17,000 s.c.f., preferably 850–14,000 s.c.f. per barrel of liquid feed.

It is of great advantage to use as high temperature as possible in order to increase the reaction rate. Temperature should, however, be kept under a certain limit according to the thermodynamic equilibrium. Use of temperatures higher than this limit indeed favors the dehydrogenation reaction rather than the hydrogenation reaction.

When the sulphur content of the charge has ben adjusted according to the desired degree of aromatic saturation, the processing may be carried out continuously for very long periods of time. The sulfur content may be lowered by hydrogenating the petroleum distillate in the presence of a catalyst comprising cobalt and molybdenum oxides supported on alumina according to processes well known in the refining of petroleum distillates.

As the reaction temperatures are relatively low, practically no coke builds up on the catalyst and it is not necessary to regenerate the catalyst by combustion. However, the catalyst activity may drop due to the accidental admission of an excessive amount of sulphur or due to a failure to admit the charge for several hours. In both cases the initial activity is restored simply by readmitting the initial charge and/or increasing the reaction temperature to 400° C., which is a temperature much higher than the thermodynamically optimum one, all the other conditions being kept constant i.e. pressure, hydrogen to hydrocarbon ratio, space velocity, these conditions being the same as for the reaction itself.

Without further elaboration, it is believed that one skilled in the art can, using the preceding description, utilize the present invention to its fullest extent. The following preferred specific embodiments are, therefore, to be construed as merely illustrative, and not limitative of the remainder of the specification and claims in any way whatsoever.

EXAMPLE 1

A petroleum distillate was hydrogen pretreated, according to a technique well known in refinery operations, in order to lower its sulphur content. Charges with various sulphur contents, mentioned hereunder, were obtained by blending treated and untreated distillates, the characteristics of which were as follows:

| | Untreated distillate | Treated distillate |
|---|---|---|
| Specific gravity 15° C./4° C | 0.787 | 0.786 |
| A.S.T.M. Distillation: | | |
| I.B.P. (° C.) | 152 | 148 |
| 2% vol | 159 | 155 |
| 5 | 162 | 159 |
| 10 | 167 | 164 |
| 20 | 172 | 169 |
| 30 | 176 | 173 |
| 40 | 180 | 177 |
| 50 | 184 | 182 |
| 60 | 189 | 187 |
| 70 | 194 | 194 |
| 80 | 203 | 202 |
| 90 | 215 | 214 |
| 95 | 225 | 224 |
| F.B.P | 233 | 234 |
| Residue, percent vol | 1.5 | 1.4 |
| Loss, percent vol | 0.3 | 0 |
| Flash Point, ° C | 42 | 38 |
| Smoke point, mm | 26 | 26 |
| Hydrocarbon analysis by fluorescent indicator adsorption (F.I.A.): | | |
| Aromatics, percent vol | 17 | 17 |
| Olefins | 0 | 0 |
| Saturated | 83 | 83 |
| Sulphur content, percent wt | 0.200 | [1] 0.0001 |

[1] 1 p.p.m.

Charges containing various amounts of sulphur, prepared as described above, were submitted to hydrogenation in a fixed bed unit under following conditions:

Space velocity: 6 v./v./hr.
Pressure: 35 kg./cm.$^2$
Temperature: 300° C.
Hydrogen to hydrocarbon ratio: 500 liters hydrogen at normal temperature and pressure (N.T.P.) per liter of liquid feed Three catalyst were tested:

Catalyst A: 0.75% platinum by weight supported on alumina;

Catalyst B: 0.75% platinum by weight supported on silica-alumina having a silica to alumina ratio of 86 to 14 by weight;

Catalyst C: 0.75% platinum by weight supported on alumina-silica added having a silica to alumina ratio of 12 to 88 by weight.

These three catalysts were formed into pellets having 3 mm. diameter and 3 mm. height.

The following table gives the percentages of aromatic hydrogenation obtained when treating charges containing various amounts of sulphur in the presence of the three catalysts, respectively.

| Sulphur content of the charge, parts per million by weight (p.p.m.) | Catalyst A, percent | Catalyst B, percent | Catalyst C, percent |
|---|---|---|---|
| 1 | 74 | 74 | 74 |
| 10 | 68 | 71 | 68 |
| 25 | 62 | 68 | 62 |
| 50 | 50 | 62 | 50 |
| 100 | 35 | 56 | 35 |
| 200 | 18 | 50 | 18 |
| 300 | 0 | 44 | 0 |

Results presented in the above table clearly demonstrate the superiority of catalyst B in resistance to the poisoning due to sulphur compounds. They show also that it is not sufficient to add only a small amount of silica in the catalyst carrier (catalyst C).

EXAMPLE 2

A charge containing 40 p.p.m. of sulphur and obtained as described in Example 1, was submitted to hydrogenation in a fixed bed of a catalyst containing 0.75% by weight of platinum on a silica-alumina carrier having a silica to alumina ratio of 86 to 14 by weight. 100 barrels of this feed per pound of catalyst were hydrogenated in a continuous manner using the following conditions:

Temperature ---------- 330° C.
Pressure ---------- 35 kg./cm.$^2$
Space velocity ---------- 20 v./v./hr.
$H_2$/hydrocarbon ---------- 500 l. $H_2$ N.T.P./1 liquid feed.

The smoke point which is easily and quickly determined is used to evaluate the degree of aromatic hydrogenation.

This hydrogenation in accordance with our invention, performed on a feed having a smoke point of 26 mm. which corresponds for this feed to an aromatic content of 17% by volume as it may be read in Example 1, leads to a product having a smoke point of 30 mm. which corresponds to an aromatic content of about 10% by volume. This example illustrates that the hydrogenation process in accordance with our invention, that is to say in the presence of a catalyst containing 0.75% by weight of platinum on a silica-alumina carrier having a silica to alumina ratio of 86 to 14 by weight and in the selected operation conditions, may be carried out in a continuous manner on a very large volume of feed without any loss of catalytic activity and with a very substantial lowering of the aromatic content of the feed.

EXAMPLE 3

It is of the utmost importance to have a catalyst capable of tolerating charges which contain accidentally a very high sulphur content, and which activity of the catalyst may be regenerated without using a complicated process such as the elimination of the impurities by combustion.

The hydrogenation of a charge containing 25 p.p.m. sulphur was started using catalyst B as in Example 1. At a space velocity of 6 v./v./hr., 35 kg./cm.$^2$, 300° C., and 500 liters N.T.P. hydrogen to 1 liter of liquid feed, the smoke point obtained was 35 mm. In order to simulate the accidental admission of a charge insufficiently pretreated, a charge containing 2,000 p.p.m. sulphur was admitted. The catalyst became posioned very rapidly, the smoke point of the product being equal to that of the feed i.e. 26 mm. The admission of the feed at 2,000 p.p.m.

sulphur was continued for 2 hours, after which the charge at 25 p.p.m. sulphur was readmitted. Soon the smoke point increased, and after 2 hours equaled the smoke point obtained initially, i.e. 35 mm. This example demonstrates that the catalyst undergoes only a temporary poisoning. It has also been found that the initial catalyst activity may be restored more rapidly if the reaction temperature is raised to 400° C. for about one hour, all the other conditions being maintained constant (pressure, space velocity and hydrogen to hydrocarbon ratio).

EXAMPLE 4

Treating at the 400° C. temperature which favors dehydrogenation rather than hydrogenation is also suitable to restore the initial catalyst activity following a drop of activity due to a feed and/or hydrogen failure for a few hours, the reactor being kept at the reaction temperature. The reason for the drop of activity under these conditions is not well understood but could be due to an accumulation of products on the catalyst. A charge containing 25 p.p.m. sulphur was treated under the conditions of Example 1 in the presence of catalyst B; the smoke point of the product was 35 mm. After 24 hours processing the liquid flow was stopped and the reactor was kept for 12 hours under hydrogen pressure. The charge was next readmitted; the smoke point of the product was only 30 mm. The temperature was then raised to 400° C. for one hour and then set back to its initial value, i.e. 300° C.; the smoke point of the product was 38 mm., thus higher than initially; after about 5 hours processing, the smoke point stabilized at the initial value, i.e. 35 mm.

This invention is particularly anaveusdtgao

This invention is particularly advantageous for the reduction of the aromatic content of jet fuel, kerosene, diesel fuel, and gas oil.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalent of the following claims.

What is claimed is:

[1. A continuous process for reducing the aromatic hydrocarbon content of a petroleum fraction boiling in the range of about 60° C. to 350° C. having a substantial sulphur content not higher than 300 parts per million by weight, which process comprises hydrogenating said fraction to obtain a substantial hydrogenation of aromatics at a temperature of about 100 to 400° C., at a pressure of about 70 to 1,000 p.s.i.g., in the presence of about 500 to 17,000 s.c.f. of hydrogen per barrel of liquid feed in contact with a catalyst comprising 0.1 to 1.0% by weight of platinum supported on an active silica-alumina carrier containing from 75 to 90% by weight of silica and at a space velocity of about 0.1 to 20 v./v./hr.]

2. The process as defined in claim [1] *10*, wherein the pressure is 300 to 800 p.s.i.g.

3. The process defined in claim [1] *10*, wherein the temperature is 250 to 350° C.

4. The process defined in claim [1] *10*, wherein the ratio of hydrogen/liquid charge is 850 to 14,000 s.c.f. $H_2$ per barrel liquid charge.

5. The process defined in claim [1] *10*, wherein the catalyst contains 0.5 to 0.8% by weight of platinum.

6. The process defined in claim [1] *10*, wherein the liquid fluid flow is in the range of 0.5 to 10 v./.v/hr.

7. The process defined in claim [1] *10*, wherein the petroleum fraction is selected from the group consisting of kerosene, diesel fuel, gas oil and jet fuel.

8. The process as defined in claim [1] *10*, wherein the catalyst temporarily in a state of reduced activity is regenerated by raising the temperature to about 400° C. for a period of about ½ to 2 hours, other conditions being maintained the same.

*9. The process as defined in claim 10 wherein the silica and alumina carrier contains about 75 to 90% by weight of silica.*

*10. A continuous process for reducing the aromatic hydrocarbon content of a petroleum fraction boiling in the range of about 60° C. to 350° C. having a substantial sulfur content of at least 10 but not higher than 300 parts per million by weight, which process comprises hydrogenating said fraction to obtain a substantial hydrogenation of aromatics at a temperature of about 100 to 400° C., at a pressure of about 70 to 1,000 p.s.i.g., in the presence of about 500 to 17,000 s.c.f. of hydrogen per barrel of liquid feed in contact with a catalyst comprising 0.1 to 1.0% by weight of platinum supported on an active silica-alumina carrier containing the silica and alumina each in substantially large porportions, silica being in major quantity, and at a space velocity of about 0.1 to 20 v./v./hr.*

*11. A continuous process for reducing the aromatic hydrocarbon content of a petroleum fraction boiling in the range of about 60° C. to 350° C. having a substantial sulfur content not higher than 300 parts per million by weight, which process comprises hydrogenating said fraction to obtain a substantial hydrogenation of aromatics at a temperature of about 100 to 400° C., at a pressure of about 70 to 1,000 p.s.i.g. in the presence of about 500 to 17,000 s.c.f. of hydrogen per barrel of liquid feed in contact with a catalyst comprising 0.1 to 1.0% by weight platinum supported on an active silica-alumina carrier containing from 70 to 90% by weight of silica and at a space velocity of about 0.1 to 20 v./v./hr.*

*12. A continuous process for reducing the aromatic hydrocarbon content of a petroleum fraction boiling in the range of about 60° C. to 350° C. having a substantial sulfur content not higher than 300 parts per million by weight, which process comprises hydrogenating said fraction to obtain a substantial hydrogenation of aromatics at a temperature of about 100 to 400° C., at a pressure of about 70 to 1,000 p.s.i.g., in the presence of about 500 to 17,000 s.c.f. of hydrogen per barrel of liquid feed in contact with a catalyst comprising 0.1 to 1.0% by weight of platinum supported on an active silica-alumina carrier containing the silica and alumina each in substantially large proportions, silica being in major quantity, and at a space velocity of about 0.1 to 20 v././hr.*

References Cited

The following references, cited by the Examiner, are of record in the patented file of this patent or the original patent.

UNITED STATES PATENTS

| | | | |
|---|---|---|---|
| 2,965,564 | 12/1960 | Kirshenbaum et al. | 208—743 |
| 3,012,961 | 12/1961 | Weisz | 260—667 |
| 3,201,345 | 8/1965 | Hamilton et al. | 208—743 |

HERBERT LEVINE, Primary Examiner

U.S. Cl. X.R.

208—144, 264